United States Patent [19]

Peters

[11] Patent Number: 4,543,416

[45] Date of Patent: Sep. 24, 1985

[54] DI(PHTHALIC ANHYDRIDE) DERIVATIVES OF DI(DISUBSTITUTED PHENOL) SULFONES

[75] Inventor: Edward N. Peters, Lenox, Mass.

[73] Assignee: General Electric Company, Pittsfield, Mass.

[21] Appl. No.: 599,732

[22] Filed: Apr. 12, 1984

Related U.S. Application Data

[62] Division of Ser. No. 462,921, Feb. 1, 1983.

[51] Int. Cl.$^4$ .......................................... C07D 307/89
[52] U.S. Cl. .................................................. 549/241
[58] Field of Search ........................................ 549/241

[56] References Cited

U.S. PATENT DOCUMENTS

| | | | |
|---|---|---|---|
| 3,383,421 | 5/1968 | Fox et al. | 260/207 |
| 3,658,938 | 4/1972 | Kochanowski et al. | 260/857 PI |
| 3,847,867 | 11/1974 | Heath et al. | 260/47 CP |
| 3,847,869 | 11/1974 | Williams | 260/47 CZ |
| 3,850,885 | 9/1980 | Takekoshi et al. | 260/47 CZ |
| 3,852,242 | 12/1974 | White | 260/47 CZ |
| 3,855,178 | 12/1974 | White et al. | 260/45.7 S |
| 3,989,670 | 11/1976 | Takekoshi et al. | 260/47 CP |
| 4,221,897 | 9/1980 | Takekoshi | 528/125 |
| 4,340,545 | 7/1982 | Webb et al. | 549/241 |
| 4,429,102 | 1/1984 | Evans et al. | 528/172 |

Primary Examiner—Richard L. Raymond
Attorney, Agent, or Firm—Bernard, Rothwell & Brown

[57] ABSTRACT

Novel di(phthalic anhydride) derivatives of di(dialkylphenol) sulfones of the following formula are disclosed:

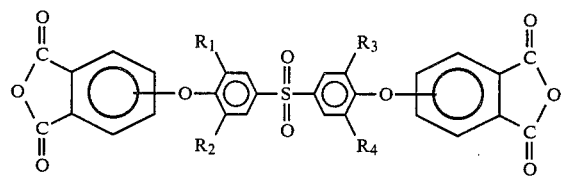

These dianhydrides can be reacted with organic diamines to form novel polyetherimide polymers having particularly beneficial properties.

4 Claims, No Drawings

DI(PHTHALIC ANHYDRIDE) DERIVATIVES OF DI(DISUBSTITUTED PHENOL) SULFONES

This is a division of application Ser. No. 462,921 filed Feb. 1, 1983.

BACKGROUND OF THE INVENTION

Polyetherimides are unique polymers which exhibit superior physical and chemical properties, including high heat resistance, exceptional strength, and excellent processibility. These polymers can be used as wire coatings and are particularly suited for injection molding applications.

A wide variety of polyetherimides and methods for their preparation have been disclosed. Generally, these polymers are prepared by reacting an organic diamine with an aromatic bis(ether dicarbonyl), i.e., an aromatic bis(ether anhydride) or an aromatic bis(ether dicarboxylic acid). For a review of polyetherimide structures and methods of preparation, see U.S. Pat. No. 3,847,867, Darrell R. Heath and Joseph G. Wirth, U.S. Pat. No. 3,847,869, Frank J. Williams III, U.S. Pat. No. 3,850,885, Tohru Takekoshi and John E. Kochanowski, U.S. Pat. No. 3,852,242, and Dwain M. White U.S. Pat. No. 3,855,178, Dwain M. White and Frank J. Williams III, all of which are incorporated herein by reference.

SUMMARY OF THE INVENTION

In accordance with the present invention, disclosed herein are di(phthalic anhydride) derivatives of di(-dialkylphenol) sulfones of the formula

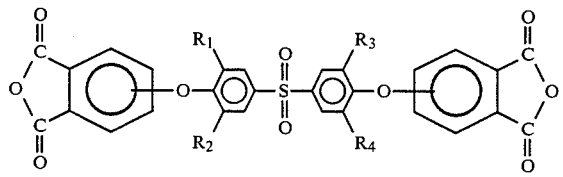

wherein each of $R_1$, $R_2$, $R_3$ and $R_4$ is independently selected from the group consisting of lower alkyl of from 1 to about 10 carbon atoms; aryl of from 6 to about 15 carbon atoms; aralkyl, wherein the alkyl portion contains from 1 to about 5 carbon atoms and the aryl portion contains from 6 to about 10 carbon atoms; halogen; lower alkoxy of from 1 to about 10 carbon atoms, and aryloxy of from 6 to about 15 carbon atoms. Also disclosed herein are novel polyetherimides prepared by reacting the above dianhydrides of the above formula with an organic diamine.

DETAILED DESCRIPTION OF THE INVENTION

The dianhydride monomers of the present invention are represented by the following formula:

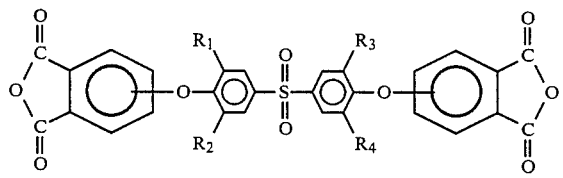

wherein each of $R_1$, $R_2$, $R_3$ and $R_4$ is independently selected from the group consisting of lower alkyl of from 1 to about 10 carbon atoms, aryl of from 6 to about 15 carbon atoms; arylalkyl, wherein the alkyl portion contains from 1 to about 5 carbon atoms and the aryl portion contains from about 6 to about 10 carbon atoms; halogen; lower alkoxy of from 1 to about 10 carbon atoms, and aryloxy of from 6 to about 15 carbon atoms.

In preferred dianhydride monomers, each of $R_1$, $R_2$, $R_3$ and $R_4$ is independently selected from the group consisting of lower alkyl of from 1 to about 4 carbon atoms, such as methyl, ethyl, propyl, and butyl; aryl of from 6 to about 10 carbon atoms, such as phenyl, tolyl, xylyl, 4-ethylphenyl, and the like; aralkyl wherein the alkyl portion contains from 1 to about 3 carbon atoms and the aryl portion contains from 6 to about 10 carbon atoms, such as benzyl, phenethyl, tolylpropyl, and the like; bromo, chloro, lower alkoxy of from 1 to about 4 carbon atoms, such as methoxy, ethoxy, propoxy, and butoxy; and aryloxy of from 6 to about 10 carbon atoms, such as phenoxy, tolyloxy, xylyloxy, and the like.

In particularly preferred dianhydride monomers, $R_1$, $R_2$, $R_3$ and $R_4$ are the same and are methyl or ethyl, preferably methyl.

The novel dianhydride monomers are advantageously prepared by reacting a di(3,5-dialkylphenol) sulfone with an N-alkylnitrophthalamide under anhydrous conditions at an elevated temperature. This reaction yields a diphthalimide of the following formula:

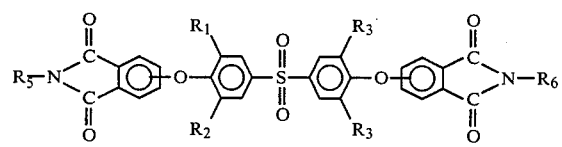

wherein $R_1$, $R_2$, $R_3$ and $R_4$ are as defined above, and $R_5$ and $R_6$ are lower alkyl, preferably methyl. The di(3,5-dialkylphenol) sulfones used as starting materials in the above reaction can be prepared by known method (for example, see U.S. Pat. No. 3,383,421 to Daniel W. Fox, et al.).

The diphthalimides can be converted to the corresponding tetracarboxylic acids by alkaline hydrolysis. A convenient means for conducting this hydrolysis is to reflux the diphthalimide in the presence of concentrated sodium hydroxide under hydrolyzing conditions. The resulting tetracarboxylic acid can be separated from the reaction mixture by precipitation following acidification with a mineral acid, such as hydrochloric acid. This tetracarboxylic acid is represented by the formula:

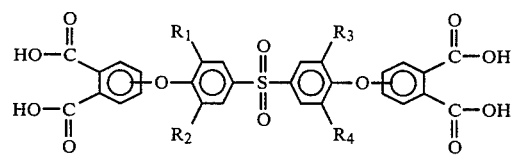

The dianhydride of the present invention can then readily be obtained by dehydration of the tetracarboxylic acid. This dehydration is advantageously accomplished by reacting the tetracarboxylic acid with acetic anhydride at an elevated temperature under dehydrating conditions. The resulting dianhydride can readily be crystallized from the reaction mixture and purified by washing with an organic solvent, such as petroleum ether, and dried.

The novel dianhydrides of this invention can be reacted with organic diamines by any of the variety of procedures known in the art to yield novel polyetherimide polymers of the following formula:

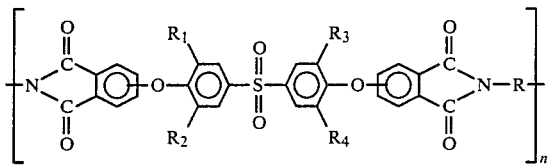

wherein $R_1$, $R_2$, $R_3$, and $R_4$ are as defined above, n is an integer in excess of 1, e.g. from 10 to about 10,000 or more and R is a divalent organic radical selected from the class consisting of (a) aromatic hydrocarbon radicals having from 6 to about 20 carbon atoms and halogenated derivatives thereof, (b) alkylene radicals and cycloalkylene radicals having from 2 to about 20 carbon atoms, $C_{(2-8)}$alkylene terminated polydiorganosiloxanes, and (c) divalent radicals included by the formula:

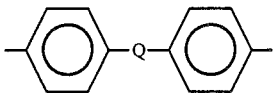

where Q is a member selected from the class consisting of:

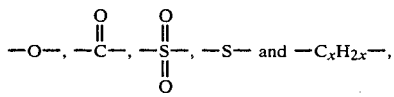

where
x is a whole number from 1 to 5 inclusive.
The organic diamines include, for example:
m-phenylenediamine,
p-phenylenediamine,
4,4'-diaminodiphenylpropane,
4,4'-diaminodiphenylmethane (commonly named 4,4'-methylenedianiline),
4,4'-diaminodiphenyl sulfide,
4,4'-diaminodiphenyl sulfone,
4,4'-diaminodiphenyl ether (commonly named 4,4'-oxydianiline),
1,5-diaminonaphthalene,
3,3'-dimethylbenzidine,
3,3'-dimethoxybenzidine,
2,4-bis(β-amino-t-butyl)toluene,
bis(p-β-amino-t-butylphenyl)ether
bis(p-β-methyl-o-aminopentyl)benzene,
1,3-diamino-4-isopropylbenzene,
1,2-bis(3-aminopropoxy)ethane,
benzidine,
m-xylylenediamine,
p-xylylenediamine,
2,4-diaminotoluene
2,6-diaminotoluene,
bis(4-aminocyclohexyl)methane,
3-methylheptamethylenediamine,
4,4-dimethylheptamethylenediamine,
2,11-dodecanediamine,
2,2-dimethylpropylenediamine,
octamethylenediamine,
3-methoxyhexamethylenediamine,
2,5-dimethylhexamethylenediamine,
2,5-dimethylheptamethylenediamine,
3-methylheptamethylenediamine,
5-methylnonamethylenediamine,
1,4-cyclohexanediamine,
1,12-octadecanediamine,
bis(3-aminopropyl)sulfide,
N-methyl-bis(3-aminopropyl)amine,
hexamethylenediamine,
heptamethylenediamine,
nonamethylenediamine,
decamethylenediamine,
bis(3-aminopropyl)tetramethyldisiloxane,
bis(4-aminobutyl)tetramethyldisiloxane, and mixtures of such diamines.

Included among the many methods of making the polyetherimides described herein are those disclosed in aforementioned United States Patents to Heath et al., Williams, Takekoshi et al., White, White et al. Although these disclosures do not teach the novel compounds of the present invention, the synthetic techniques and reactions described therein can be used for preparing the polyetherimides of this invention. These disclosures are, therefore, incorporated herein in their entirety by reference for the purpose of teaching, by way of illustration, general and specific methods for preparing the polyetherimides of this invention.

Polyetherimide polymers prepared from the novel dianhydrides described herein have been found to have certain beneficial properties over previously known polyetherimides. In addition to excellent thermal stability, mechanical strength, and processability, which are inherent in polyetherimides of this general class, the present polyetherimides have also been found to have exceptionally high glass transition temperatures. For example, in polyetherimides described above wherein $R_1$, $R_2$, $R_3$ and $R_4$ are each methyl and R is p-phenylene, the glass transition temperature has been found to be about 300° C., which is substantially higher than that of previously known polyetherimides. This high glass transition temperature permits the use of the polyetherimide polymer in structural applications where high heat resistance is a prerequisite.

The present invention is further illustrated by the following examples which are not intended to be limiting.

EXAMPLE I

To a four-neck reaction vessel equipped with a mechanical stirrer, thermometer, reflux condenser/Dean-Stark water trap, and heating means was added 306.37 grams (1.00 moles) di(3,5-dimethylphenol)sulfone, 80 grams of 50% aqueous sodium hydroxide (200 moles), 400 ml dimethylsulfoxide, and 675 ml chlorobenzene. Under nitrogen the mixture was heated to 135° C. and stirred until the azeotropic removal of water was complete. The temperature was raised to 150° C. by distilling of chlorobenzene. The mixture was cooled to 60° C. and 412.32 grams (2.00 moles) of N-methyl-4-nitrophthalimide was added. The reaction mixture was stirred for 12 hours at about 60° C. Upon cooling the product fell out of solution and was isolated by filtration. The crystals were washed with water and then methanol. The product was dried in a vacuum oven at 80° C. for about 18 hours to give 555.9 grams of the bis(N-methylimide) of di(3,5-dimethylphenol)sulfone. the material exhibited 99% purity by high pressure liquid chromatography. The melting point was 280°-282° C.

EXAMPLE II

About 300 grams (0.480 moles) of the bisimide produced by the procedure of Example I was added to a reaction vessel equipped with a reflux condenser together with 400 grams of 50% sodium hydroxide and 800 ml water. The mixture was heated at its reflux temperature for 18 hours, cooled to room temperature and acidified with an excess of 1N hydrochloric acid. The tetraacid precipitated out of solution and was isolated by filtration. The filter cake was washed with water. The product thus obtained was dried for about 18 hours in a vacuum oven at 80° C. to give 279.2 grams of the corresponding tetraacid having the formula

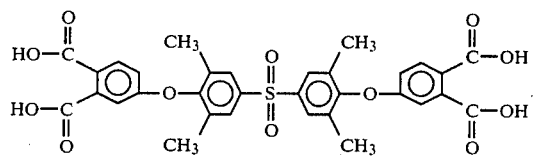

EXAMPLE III

A mixture of 250 grams (0.394 moles) of the tetraacid together with 1000 ml acetic acid and 150 grams acetic anhydride was heated at the reflux temperature of the mass and stirred for about 24 hours and cooled to room temperature. The dianhydride crystallized readily and was filtered. The filter cake was washed with petroleum ether and traces of solvent removed in a vacuum oven at 80° C. to give 209.9 grams of the desired formula having a melting point of 288°-290° C.

EXAMPLE IV

In a 500 ml four necked flask equipped with Dean Stark trap/condenser, mechanical stirrer, nitrogen inlet and thermometer was added 29.93 g (0.050 moles) of the dianhydride produced by the procedure of Example III, 5.41 g (0.050 moles) m-phenylenediamine, 0.14 g (0.001 moles) phthalic anhydride, 150 ml m-cresol, and 100 ml toluene. The mixture was heated under nitrogen at 100° C. for 30 minutes, followed by raising the temperature to 150° C., during which the water formed from the reaction was removed by azeotropic distillation. After about 4 hours, the temperature was inceased to 180° C. and held there for one hour, then cooled to room temperature. The viscous mixture was diluted with 100 ml of chloroform and the polymer isolated by precipitation in methanol. The precipitate was dreid at 125° C. to yield a polyetherimide polymer composed of repeating units of the following structure:

The polymer had an intrinsic viscosity of 0.65 dl/gm when measured in phenol/tetrachloroethane (60/40, w/w), and a glass transition temperature of 302° C.

EXAMPLE V

A polyetherimide was prepared in accordance with the procedure of Example IV, except as noted hereafter. The reactants and solvents were 4.50 grams (0.00752 moles) of the dianhydride described in Example III, 0.88 grams (0.00749 moles) hexamethylenediamine, 0.02 grams (0.000135 moles) phthalic anhydride, 30 ml m-cresol, and 20 ml toluene. The mixture was slowly heated to 170° C. for 16 hours, cooled to room temperature, diluted with 50 ml chloroform, and added to methanol to precipitate the polymer. The precipitate was dried at 125° C. to give 4.6 grams of polymer which had an intrinsic viscosity of 0.48 dl/g and a glass transition temperature of 190° C.

EXAMPLE VI

A polyetherimide was prepared in accordance with the procedure of Example IV, except as noted hereafter. The reactants and solvents were 6.00 grams (0.010 moles) of the dianhydride described in Example III, 1.98 grams (0.00999 moles) methylenedianiline, 0.03 grams, (0.000203 moles) phthalic anhydride, 30 ml m-cresol, and 20 ml toluene. The mixture was heated to 170° C. for 8 hours, cooled to room temperature, diluted with 50 ml chloroform, and added to methanol to precipitate the polymer. The precipitate was dried at 125° C. to give 7.3 grams of polymer which had an intrinsic viscosity of 0.57 dl/g and a glass transition temperature of 289° C.

EXAMPLE VII

A polyetherimide was prepared in accordance with the procedure of Example IV, except as noted hereafter. The reactants and solvents were 3.00 grams (0.00501 moles) of the dianhydride described in Example III, 2.60 grams (0.00500 moles) of bisphenol A dianhydride, 0.03 (0.000203 moles) phthalic anhydride, 1.31 g (0.0121 moles) m-phenylenediamine, 30 ml m-cresol, and 20 ml toluene. The mixture was heated to 170° C. for 12 hours, cooled to room temperature, diluted with 50 ml chloroform, and added to methanol to precipitate the polymer. The precipitate was dried at 125° C. to give 5.8 grams of polymer which had an intrinsic viscosity of 0.56 dl/g and a glass transition temperature of 258° C.

EXAMPLE VIII

The procedure of Examples I-IV are repeated in all essential details, except that the sulfone starting material employed in Example I is di(3,5-diisopropylphenol)sulfone. The resulting polyetherimde polymer is composed of repeating units of the following structure:

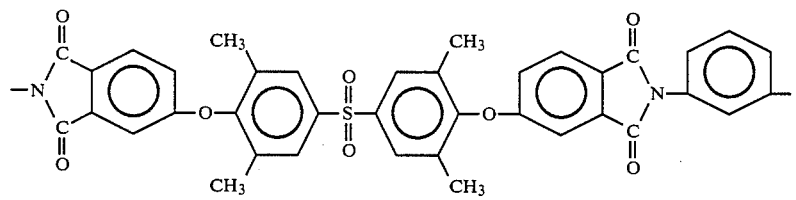

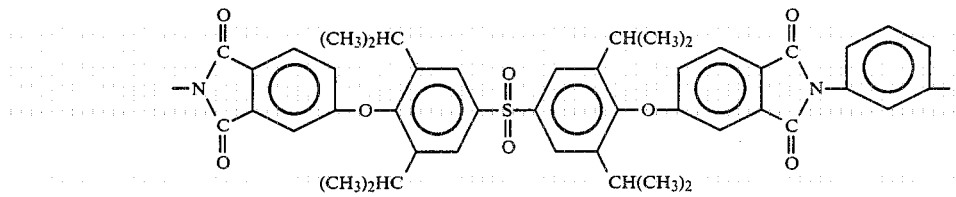

EXAMPLE IX

The procedure of Examples I–IV are repeated in all essential details, except that the sulfone starting material employed in Example I is di(3,4-diphenylphenol)sulfone. The resulting polyetherimide polymer is composed of repeating units of the following structure:

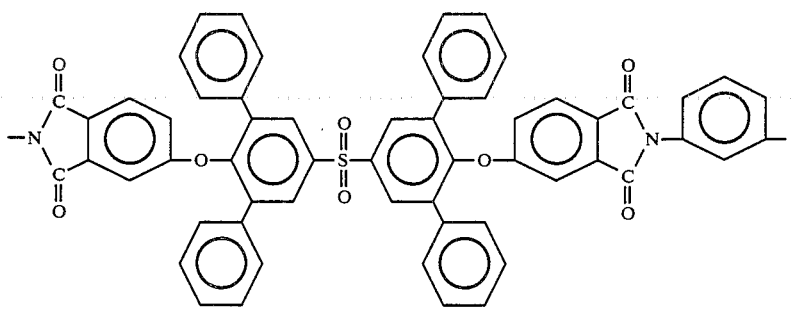

EXAMPLE X

The procedures of Examples I–IV are repeated in all essential details except that the sulfone starting material employed in Example I is di(3,4-dibromophenol)sulfone. The resulting polyetherimide polymer is composed of repeating units of the following structure:

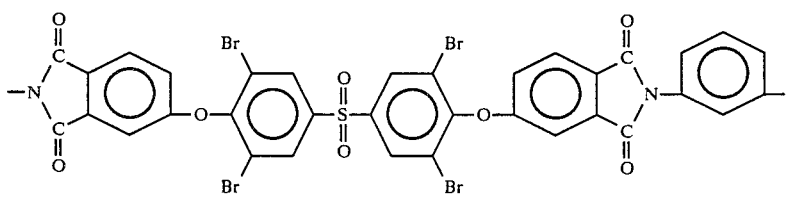

EXAMPLE XI

The procedures of Examples I–IV are repeated in all essential details except that the sulfone starting material employed in Example I is di(3-chloro-5-benzyloxyphenol)sulfone. The resulting polyetherimide polymer is composed of repeating units of the following structure:

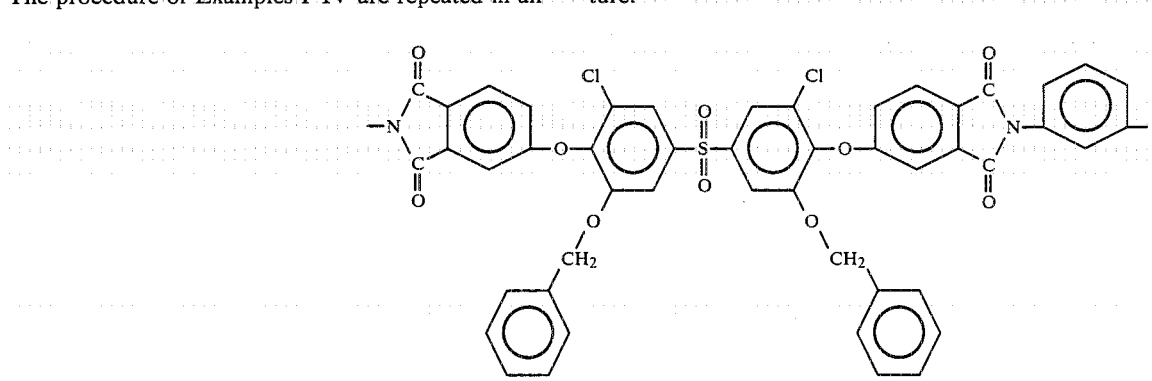

I claim:

1. A compound of the formula

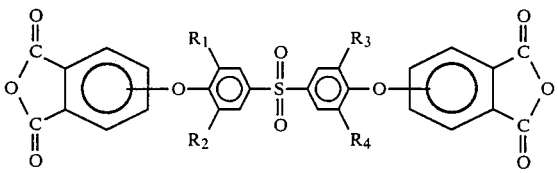

wherein $R_1$, $R_2$, $R_3$ and $R_4$ independently selected from the group consisting of lower alkyl of from 1 to about 10 carbon atoms; aryl of from 6 to about 15 carbon atoms; aralkyl, wherein the alkyl portion contains from 1 to about 5 carbon atoms and the aryl portion contains from 6 to about 10 carbon atoms; halogen; lower alkoxy of from 1 to about 10 carbon atoms, and aryloxy of from 6 to about 15 carbon atoms.

2. The compound of claim 1, wherein each of $R_1$, $R_2$, $R_3$ and $R_4$ is independently selected from the group consisting of lower alkyl of from 1 to about 4 carbon atoms; aryl of from 6 to about 10 carbon atoms; aralkyl wherein the alkyl portion contains from 1 to about 3 carbon atoms and the aryl portion contains from 6 to about 10 carbon atoms; bromo, chloro, lower alkoxy of from 1 to about 4 carbon atoms; and aryloxy of from 6 to about 10 carbon atoms.

3. The compound of claim 1, wherein $R_1$, $R_2$, $R_3$, and $R_4$ are the same, and are methyl or ethyl.

4. The compound of claim 3, wherein $R_1$, $R_2$, $R_3$, and $R_4$ are each methyl.

* * * * *